(12) United States Patent
Tuke et al.

(10) Patent No.: US 6,869,448 B2
(45) Date of Patent: Mar. 22, 2005

(54) PROSTHESIS

(75) Inventors: Michael Anthony Tuke, Guildford (GB); Robert Michael Wozencroft, Epsom (GB); Andrew Clive Taylor, Chichester (GB)

(73) Assignee: Finsbury (Development) Limited, Leatherhead (GB)

( * ) Notice: Subject to any disclaimer, the term of this patent is extended or adjusted under 35 U.S.C. 154(b) by 74 days.

(21) Appl. No.: 10/341,618

(22) Filed: Jan. 14, 2003

(65) Prior Publication Data

US 2003/0139817 A1 Jul. 24, 2003

(30) Foreign Application Priority Data

Jan. 18, 2002 (GB) .............................................. 0201149

(51) Int. Cl.$^7$ .................................................. A61F 2/38
(52) U.S. Cl. .................................. 623/20.32; 623/20.14
(58) Field of Search ............................. 623/20.28–20.33

(56) References Cited

U.S. PATENT DOCUMENTS

| 3,868,730 A | 3/1975 | Kaufer et al. |
| 3,958,278 A | 5/1976 | Lee et al. |
| 4,016,606 A | 4/1977 | Murray et al. |
| 4,207,627 A | 6/1980 | Cloutier |

(List continued on next page.)

FOREIGN PATENT DOCUMENTS

| EP | 0 495 340 A1 | 12/1991 |
| FR | 2 700 262 A1 | 7/1994 |

OTHER PUBLICATIONS

Bert, MD, et al., "The Incidence of Modular Tibial Polyethylene Insert Exchange in Total Knee Arthroplasty When Polyethylene Failure Occurs", The Journal of Arthroplasty, © 1998 by Churchill Livingstone®, pp. 609–614, vol. 13, No. 6, St. Paul, MN.

Bugbee, MD, et al., "4–to 10—Year Results With The Anatomic Modular Total Knee", Clinical Orthopaedics and Related Research, © 1998 Lippincott—Raven Publishers, pp. 156–165, No. 348, Alexandria, Virginia.

Engh, MD, et al., "In Vivo Deterioration Of Tibial Baseplate Locking Meschanisms in Contemporary Modular Total Knee Components", Copyright © 2001 By The Journal Of Bone And Joint Sugery, Incorporated, pp. 1660–1665, Investigation Performed At The Anderson Orthopaedic Research Institute, Alexandria, Virgina.

Parks, MS, et al., "Modular Tibial Insert Micromotion", Clinical Orthopaedics and Related Research, © 1998 Lippincott Williams & Wilkins, pp. 10–15, No. 356, Alexandria, Virginia.

(List continued on next page.)

*Primary Examiner*—Corrine McDermott
*Assistant Examiner*—Thomas Barrett
(74) *Attorney, Agent, or Firm*—Senniger Powers

(57) ABSTRACT

A tibial prosthesis has a metal tray component (1) comprising a transverse member (3) with a peripheral upstanding rim (6) and a projecting stem (4). The upstanding rim (6) includes a posterior rim portion with an undercut lip forming a pair of recesses (7, 8) and an anterior rim portion with an open angled posterior surface portion (9) and a posteriorly projecting barbed portion (10). The prosthesis also includes a tibia insert (2) made of a plastics material which fits on the tibial implant (1) within the upstanding rim (6) and has on a posterior portion thereof a shaped contour (14, 15) adapted in use to fit snugly under the undercut lip and on an anterior portion thereof an anterior surface (13) having a taper angle substantially corresponding to the angle of the open angled posterior surface portion.

7 Claims, 2 Drawing Sheets

U.S. PATENT DOCUMENTS

| | | |
|---|---|---|
| 4,216,549 A | 8/1980 | Hillberry et al. |
| 4,219,893 A | 9/1980 | Noiles |
| 4,257,129 A | 3/1981 | Volz |
| 4,462,120 A | 7/1984 | Rambert et al. |
| 4,470,158 A | 9/1984 | Pappas et al. |
| 4,550,448 A | 11/1985 | Kenna |
| 4,673,407 A | 6/1987 | Martin |
| 4,673,408 A | 6/1987 | Grobbelaar |
| 4,711,639 A | 12/1987 | Grundei |
| 4,714,474 A | 12/1987 | Brooks, Jr. et al. |
| 4,795,468 A | 1/1989 | Hodorek et al. |
| 4,822,362 A | 4/1989 | Walker et al. |
| 4,936,853 A | 6/1990 | Fabian et al. |
| 4,938,769 A | 7/1990 | Shaw |
| 4,944,757 A | 7/1990 | Martinez et al. |
| 4,950,298 A | 8/1990 | Gustilo et al. |
| 4,963,152 A | 10/1990 | Hofmann et al. |
| 5,007,933 A | 4/1991 | Sidebotham et al. |
| 5,062,852 A | 11/1991 | Dorr et al. |
| 5,080,675 A | 1/1992 | Lawes et al. |
| 5,108,442 A | 4/1992 | Smith |
| 5,192,328 A | 3/1993 | Winters |
| 5,194,066 A | 3/1993 | Van Zile |
| 5,344,460 A | 9/1994 | Turanyi et al. |
| 5,370,699 A | 12/1994 | Hood et al. |
| 5,405,396 A | 4/1995 | Heldreth et al. |
| 5,458,637 A | 10/1995 | Hayes |
| 5,645,604 A | 7/1997 | Schneider et al. |
| 5,702,463 A | 12/1997 | Pothier et al. |
| 5,702,464 A | 12/1997 | Lackey et al. |
| 6,126,692 A | 10/2000 | Robie et al. |
| 6,569,202 B2 * | 5/2003 | Whiteside ................ 623/20.32 |

OTHER PUBLICATIONS

Peters, Jr., MD, et al., "Osteolysis after Total Knee Arthroplasty without Cement", Copyright 1992 By The Journal Of Bone And Joint Sugery, Incorporated, pp. 864–876, Arlington, Virginia.

Rosenberg, MD, et al., "A Comparison of Cemented and Cementless Fixation with the Miller–Galante Total Knee Arthroplasty", Surgical Reconstruction of the Arthritic Knee I, Jan. 1989, pp. 97–110, vol. 20, No. 1, Orthopedic Clinics of North America.

Wasielewski, MS, MD, et al., "Tibial Insert Undersurface as a Contributing Source of Polyethylene Wear Debris", Clinical Orthopaedics and Related Research, © 1997 Lippincott—Raven Publishers, pp. 53–59, No. 345.

Whiteside, MD, "Clinical Results of Whiteside Ortholoc Total Knee Replacement", Surgical Reconstruction of the Arthritic Knee I, Jan. 1989, pp. 113–124, vol. 20, No. 1, Orthopedic Clinics of North America.

* cited by examiner

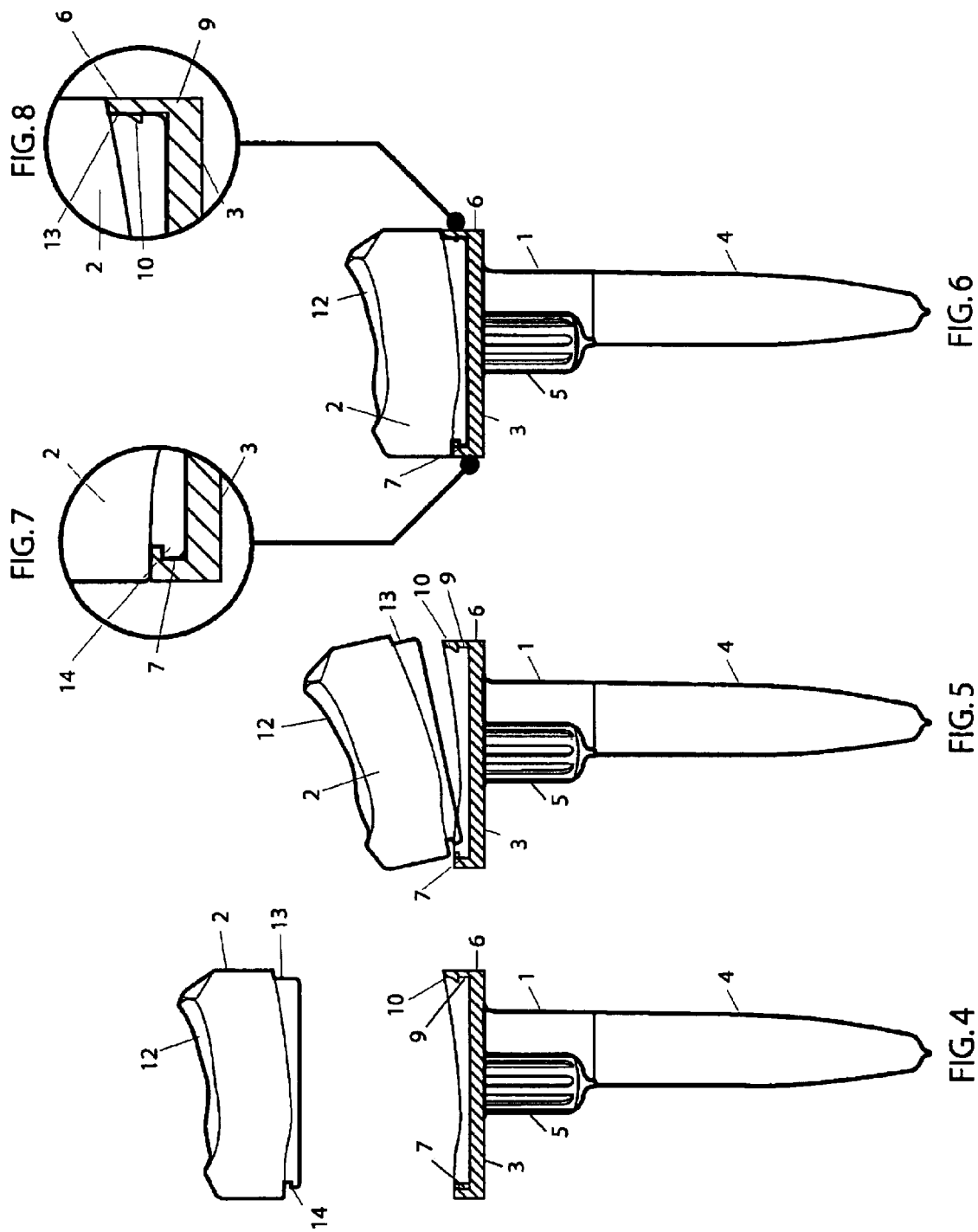

US 6,869,448 B2

PROSTHESIS

BACKGROUND OF THE INVENTION

This invention relates to a tibial prosthesis for implantation in a surgically prepared cavity in a tibia of a patient undergoing knee replacement.

Tibial prostheses are commonly made in two parts, namely a metal tray-shaped component with a stem projecting from a lower side thereof for insertion in a surgically prepared cavity in a tibia of a patient requiring a tibial surface replacement operation and with an upstanding peripheral rim and a tibia insert which is typically made from ultra high molecular weight polyethylene that fits on top of the tray component and is located in place inter alia, by means of the upstanding peripheral rim.

There are typically 6 sizes of the metal tray-shaped component to account for variations in tibia bone size and 5 thicknesses of tibia insert to account for variation in the amount of bone resected and laxity of the collateral ligaments. Tibia inserts typically also come in 2 or 3 sizes to best fit the range of metal tray sizes. Tibia size and insert thickness are unrelated; therefore there are many possible combinations of assembled components, depending on the specific surgical requirements.

Various locking arrangements for locking the tibia insert in place on top of the metal tray portion have been proposed. Thus many total and uni-compartmental knee replacements have a clip mechanism to fit the insert to the tray, which the surgeon assembles, as a modular series of parts. However, the existing clip mechanisms have the disadvantage that, since the tibia insert is merely clipped into place, there is room for motion since only the clip portion of the tibia insert resists such motion. Thus, although the surgeon may feel the insert clip into place and it may seem that the insert is not moving easily, such mechanisms do in fact allow relative movement between the tray and insert when the prosthesis is loaded as the patient walks or takes other exercise after implantation has been effected. Such motion causes so-called "backside wear" which exacerbates the phenomenon of debris-induced osteolysis. The effects of modular tibial insert micromotion have been reported, for example, by Nancy L. Parks et al., Clinical Orthopaedics and Related Research, Number 356, pages 10 to 15 (1998). Other papers highlighting the problems of existing tibial prostheses include those by Gerard A. Engh et al., The Journal of Bone and Joint Surgery, Volume 83-A, Number 11, November 2001, pages 1660 to 1665; Ray C. Wasielski et al., Clinical Orthopaedics and Related Research, Number 345, pages 53 to 59 (1997); Jack M. Bert et al., The Journal of Arthroplasty, Volume 13, No. 6 (1998), pages 609 to 614; William D. Bugbee et al., Clinical Orthopaedics and Related Research, Number 348, pages 158 to 165 (1998); Paul A. Peters et al., The Journal of Bone and Joint Surgery, Vol. 74-A, No. 6 (July 1992), pages 864 to 876; Aaron G. Rosenberg et al., Orthopedic Clinics of North America, Vol. 20, No. 1 (January 1989(, pages 97 to 110; and Leo A. Whiteside, Orthopedic Clinics of North America, Vol. 20, No. 1 (January 1989), pages 113 to 124.

A few designs of tibial prostheses are sold in the form of compression moulded plastics material units and metal backs which are assembled as one piece units in the factory. However, although such moulded one piece knee components overcome the problems associated with micromotion, a significant drawback to their widespread use is the problem of storing the large volume of stock that must be held by a hospital due to the need for all size and thickness options being required on the shelf for each operation.

On the other hand the systems which allow the surgeon to clip together a tibia and a tray avoid this storage problem by allowing choice of many variants of metal tray and tibia insert.

There is a large volume of patent literature describing tibial prostheses, including U.S. Pat. No. 5,080,675 (Lawes et al.), U.S. Pat. No. 4,944,757 (Martinez et al.), U.S. Pat. No. 4,938,769 (Shaw), U.S. Pat. No. 4,936,853 (Fabian et al.), U.S. Pat. No. 4,714,474 (Brooks, Jr. et al.), U.S. Pat. No. 4,711,639 (Grundei), U.S. Pat. No. 4,257,129 (Volz), U.S. Pat. No. 4,219,893 (Noiles), U.S. Pat. No. 4,207,627 (Cloutier), U.S. Pat. No. 4,016,606 (Murray et al.), U.S. Pat. No. 6,126,692 (Robie et al.), U.S. Pat. No. 5,702,464 (Lackey et al.), U.S. Pat. No. 5,702,463 (Pothier et al.), U.S. Pat. No. 5,645,604 (Schneider et al.), U.S. Pat. No. 4,950,298 (Gustilo et al.), U.S. Pat. No. 5,370,699 (Hood et al.), U.S. Pat. No. 4,795,468 (Hodorek et al.), U.S. Pat. No. 4,673,408 (Grobbelaar), U.S. Pat. No. 4,550,448 (Kenna), U.S. Pat. No. 5,458,637 (Hayes), U.S. Pat. No. 5,405,396 (Heldreth et al.), U.S. Pat. No. 5,344,460 (Turanyi et al.), U.S. Pat. No. 5,194,066 (Van Zile), U.S. Pat. No. 5,192,328 (Winters), U.S. Pat. No. 5,108,442 (Smith), U.S. Pat. No. 5,062,852 (Dorr et al.), U.S. Pat. No. 5,007,933 (Sidebotham et al.), U.S. Pat. No. 4,963,152 (Hofmann), U.S. Pat. No. 4,822,362 (Walker et al.), U.S. Pat. No. 4,673,407 (Martin), U.S. Pat. No. 4,470,158 (Pappas et al.), U.S. Pat. No. 4,462,120 (Rambert et al.), U.S. Pat. No. 4,216,549 (Hillberry et al.), U.S. Pat. No. 3,958,278 (Lee et al.), and U.S. Pat. No. 3,868,730 (Kaufer et al.).

There is a need in the art for a tibial prosthesis formed from a metal tray component and a plastics material tibia insert which can be assembled in an operating theatre by a surgeon in the course of a total or partial knee replacement operation and which will, after assembly and implantation in a patient's knee, substantially obviate the problems of micromotion between the two components of the prosthesis and potential exacerbation of debris-induced osteolysis.

SUMMARY OF THE INVENTION

The present invention accordingly seeks to provide a two part tibial prosthesis suitable for assembly by a surgeon prior to surgical implantation in a patient which will substantially avoid the risk of micromotion occurring between the tibia insert and the tray component after implantation and which will minimise subsequent debris formation due to wear as the patient subsequently walks and takes other exercise.

According to the present invention there is provided a tibial prosthesis for implantation in a surgically prepared substantially axial cavity in a tibia of a patient comprising:

a metal tray component comprising a transverse member adapted in use to extend substantially transverse to the axis of the surgically prepared cavity, the transverse member having an upper side with a peripheral upstanding rim and a lower side provided with a projecting stem for insertion in the surgically prepared cavity, the upstanding rim including a posterior rim portion and an anterior rim portion, the posterior rim portion being provided with an undercut lip portion and the anterior rim portion having an open angled posterior surface portion and a posteriorly projecting barbed portion; and a tibia insert made of a plastics material shaped to fit on the upper side of the tibial implant within the upstanding rim and having an upper bearing surface adapted to cooperate with at least one condyle of a femur or of a femoral implant and a lower surface, the tibia insert further having on a posterior portion thereof a shaped contour adapted in use to fit snugly under the undercut lip and on an anterior portion thereof an anterior surface having a taper angle substantially corresponding to the angle of the open angled posterior surface portion;

whereby, in use, a surgeon can insert the tibia insert in the metal tray component by first locating the shaped contour under the undercut lip and then pressing on the upper bearing surface to force the anterior surface into engagement with the open angled posterior surface portion, to cause it to interface with the barbed portion so as to lock the tibia insert to the metal tray component, and to minimise translational micromotion.

The tray component and tibia insert may together comprise a total tibial prosthesis. Alternatively they may together comprise a unicompartmental tibial prosthesis.

In a particularly preferred tibial prosthesis the undercut lip portion defines at least one recess and the shaped contour comprises at least one corresponding lug adapted for receipt in a corresponding recess.

Typically the taper angle ranges from about 2° to about 10°.

The open angled posterior surface portion preferably extends around at least a substantial portion of the anterior part of the rim. That anterior part can be considered as extending anterior to a line joining those points on the interior surface of the rim which are farthest apart measured in a medial-lateral direction. Typically the open angled posterior surface portion extends for at least about half way, preferably at least two thirds, and even more preferably at least three quarters of the way along that anterior part.

It is also preferred that the posteriorly projecting barbed portion preferably extends along a substantial portion of the peripheral length of the open angled posterior surface portion.

In order that the invention shall be clearly understood and readily carried into effect, a preferred embodiment thereof will now be described, by way of example only, with reference to the accompanying drawings, wherein:

BRIEF DESCRIPTION OF THE DRAWINGS

FIGS. 4 to 6 are side views partly in section through the total tibial prosthesis of FIGS. 1 to 3 illustrating various stages during insertion of the tibia insert into the metal tray component; and FIGS. 7 and 8 are sectional views on an enlarged scale of the posterior and anterior portions respectively of a peripheral rim forming part of the metal tray component illustrated in FIG. 6.

DETAILED DESCRIPTION OF THE PREFERRED EMBODIMENT

Figure 3:
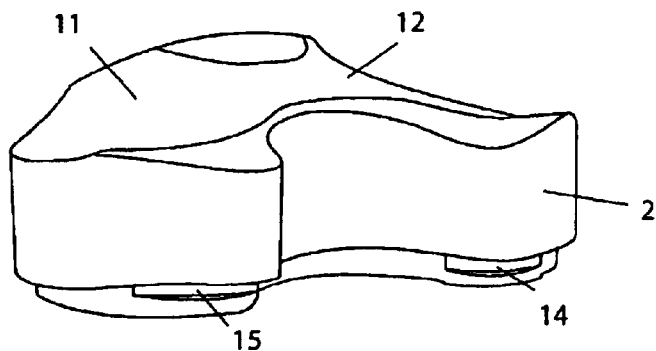
FIG. 3 is a perspective posterior view of a tibia insert which also forms part of the preferred form of total tibial prosthesis of the invention.
Figure 2:
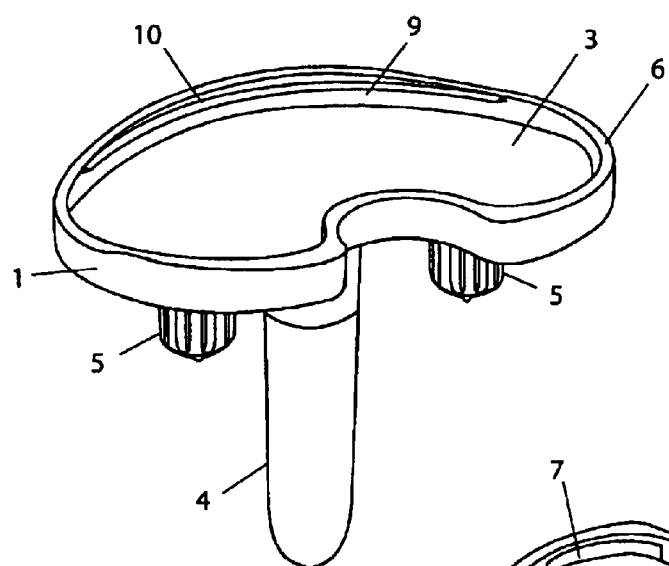
FIG. 2 is a similar perspective posterior view of the metal tray component of FIG. 1.
Figure 1:
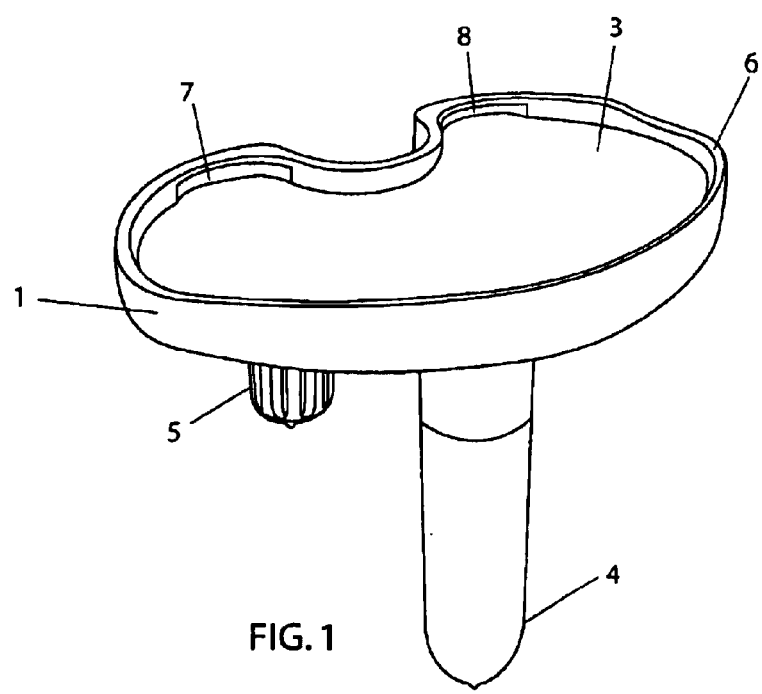
FIG. 1 is a perspective anterior view of a metal tray component forming part of a preferred form of total tibial prosthesis constructed in accordance with the invention.

Referring to the drawings, and to FIGS. 1 to 3 in particular, a total tibial prosthesis according to the invention comprises a metal tray component 1, which is made from a suitable biocompatible metal or alloy, such as stainless steel, nickel-cobalt, titanium or a titanium alloy, and a tibia insert 2 made of a suitable plastics material, such as ultra high molecular weight polyethylene. Tray component 1 comprises a transverse member in the form of a generally flat plate 3 from the underside of which projects a stem 4 and two pegs 5. Stem 4 is intended for receipt in a surgically prepared cavity that extends substantially parallel to the axis of a tibia of a patient into whom the tibial prosthesis is to be implanted and is formed in a resected face of the tibia, while pegs 5 are intended for receipt in corresponding further smaller axial cavities in the resected tibia. Surrounding the plate 3 is a upstanding peripheral rim 6. The posterior portion of rim 6 is undercut in two places so as to provide recesses 7, 8. An anterior portion of the peripheral rim 6 immediately opposite the recesses 7, 8 is open angled with a rake of between about 2° and about 10° so that the posterior surface 9 (see also FIG. 8) of that anterior portion of the peripheral rim makes an angle of from about 92° to about 100° with the flat top surface of plate 3. That posterior surface 9 is further provided with a long barb 10 for a purpose which will be explained hereafter. Posterior surface 9 extends for a substantial distance around the rim 6 and preferably at least around a majority of the anterior half of the rim (i.e. the part of the rim anterior to a line joining those points on the interior surface of the rim 6 which are farthest apart measured in a medial-lateral direction).

Tibia insert 2 is provided on its upper side with bearing surfaces 11, 12 for respective condyles on a corresponding femoral prosthesis (not shown) or on the patient's own femur. Its underside is shaped so as to fit snugly on top of plate 3 within the peripheral rim 6. The tolerances on tibia insert 2 and tray component 1 are so chosen that there is a nominal or controlled interface fit between the two components of the tibial prosthesis when tibia insert 2 is fully seated on tray component 1. Thus an anterior portion 13 of tibia insert 2 is provided with an anterior surface with a taper angle that exactly matches the angle of posterior surface 9. The posterior part of tibia insert 2 is provided with a pair of lugs 14, 15 which are designed to be received in recesses 7 and 8 respectively.

The long barb 10 interfaces with the front surface 13 of tibia insert 2 when the latter is pushed fully home within the upstanding rim 6 of tray component 1.

The assembly of tibia insert 2 to tray component 1 by a surgeon is illustrated further in FIGS. 4 to 8. The posterior of tibia insert 2 is presented to the anterior face of the posterior portion of peripheral rim 6 of tray component 1 so that the lugs 14, 15 enter recesses 7, 8 as shown in FIG. 5. Then the anterior portion of tibia insert 2 is pushed fully home into the recess formed by rim 6 on top of plate 3. A press-like instrument (not shown) may be provided to assist the surgeon in fitting and pressing the tibia insert 2 fully home. Since the tray component 1 has an open angled rim 6 and the anterior portion of tibia insert 2 has an anterior surface 13 with a corresponding taper angle, the insert 2 is initially loose and thus readily able to enter the cavity within the rim 6 on top of plate 3 but progressively the fit becomes tighter and tighter as the tibia insert 2 encounters the surface 9. At the same time barb 10 commences to interface with the tibia insert 2 and to cause local deformation of the material of tibia insert 2. The barb 10 in effect provides a net interference with the volume of tibia insert 2 so that the insert 2 is squeezed in the anterior-posterior direction and to a lesser degree in the medial-lateral direction. The two mating components 1, 2 are designed so that, when fully assembled, there are no significant voids allowing translational micromotion. The result of this and the component tolerance may induce a small designed lift-off of the tibia insert 2 from the tray floor (i.e. the upper surface of plate 3) but this is of little concern since the patient's body weight will act to close the resulting space with little creep taking place of the ultra high molecular weight polyethylene from which tibia insert 2 is made.

The illustrated tibial prosthesis of FIGS. 1 to 8 is a total tibial prosthesis. It will be readily apparent to those skilled in the art that the teachings of the invention are equally applicable to a unicompartmental tibial prosthesis and that it is intended that the invention shall also extend to such unicompartmental tibial prostheses.

What is claimed is:

1. A tibial prosthesis for implantation in a surgically prepared substantially axial cavity in a tibia of a patient comprising:

a metal tray component comprising a transverse member adapted in use to extend substantially transverse to the axis of the surgically prepared cavity, the transverse member having an upper side with a peripheral upstanding rim and a lower side provided with a projecting stem for insertion in the surgically prepared cavity, the upstanding rim including a posterior rim portion and an anterior rim portion, the posterior rim portion being provided with an undercut lip portion and the anterior rim portion having an open angled posterior surface portion and a posteriorly projecting barbed portion; and a tibia insert made of a plastics material shaped to fit on the upper side of the tibial implant within the upstanding rim and having an upper bearing surface adapted to cooperate with at least one condyle of a femur or of a femoral implant and a lower surface, the tibia insert further having on a posterior portion thereof a shaped contour adapted in use to fit snugly under the undercut lip and on an anterior portion thereof an anterior surface having a taper angle substantially corresponding to the angle of the open angled posterior surface portion;

wherein the tibia insert is adapted to be inserted in the metal tray component by first locating the shaped contour under the undercut lip and then pressing on the upper bearing surface to force the anterior surface into engagement with the open angled posterior surface portion, to cause the tibia insert to interface with the barbed portion and to provide a net interference with the tibia insert so as to lock the tibia insert to the metal tray component, and to minimise translational micromotion.

2. A tibial prosthesis according to claim 1, in which the tray component and tibia insert together comprise a total tibial prosthesis.

3. A tibial prosthesis according to claim 1, in which the tray component and the tibia insert together comprise a unicompartmental tibial prosthesis.

4. A tibial prosthesis according to claim 1, in which the undercut lip portion defines at least one recess and in which the shaped contour comprises at least one corresponding lug adapted for receipt in a corresponding recess.

5. A tibial prosthesis according to claim 1, in which the taper angle ranges from about 2° to about 10°.

6. A tibial prosthesis according to claim 1, in which the open angled posterior surface portion extends around at least a substantial portion of the anterior part of the rim.

7. A tibial prosthesis according to claim 1, in which the posteriorly projecting barbed portion extends along a substantial portion of the peripheral length of the open angled posterior surface portion.

* * * * *